United States Patent [19]
Allington, deceased et al.

[11] 4,159,933
[45] Jul. 3, 1979

[54] SAMPLE CONCENTRATOR

[75] Inventors: William B. Allington, deceased, late of Lincoln, Nebr., by Richard T. Emery, executor; James W. Nelson, Lincoln, Nebr.; Arthur L. Cordry, Lincoln, Nebr.; Gail A. McCullough, Lincoln, Nebr.; Don E. Mitchell, Lincoln, Nebr.

[73] Assignee: Instrumentation Specialties Company, Lincoln, Nebr.

[21] Appl. No.: 781,176

[22] Filed: Mar. 25, 1977

[51] Int. Cl.$^2$ .................... G01N 27/40; G01N 27/26; G01N 27/28

[52] U.S. Cl. .......................... 204/180 R; 204/180 S; 204/180 P; 204/180 G; 204/299 R; 424/12

[58] Field of Search .............. 204/180 G, 299, 180 R, 204/180 S, 180 P; 23/230 B; 424/12

[56] References Cited

U.S. PATENT DOCUMENTS

| 3,470,080 | 9/1969 | Raymond et al. | 204/180 G |
| 3,533,933 | 10/1970 | Strauch | 204/180 G |
| 3,579,433 | 5/1971 | Dahlgren | 204/180 G X |
| 3,616,454 | 10/1971 | Levy et al. | 204/180 G X |
| 3,640,813 | 2/1972 | Nerenberg | 204/180 G X |
| 3,674,678 | 7/1972 | Post, Jr. et al. | 204/299 |
| 3,720,593 | 3/1973 | Juhos | 204/180 G |

*Primary Examiner*—Arthur C. Prescott
*Attorney, Agent, or Firm*—Vincent L. Carney

[57] ABSTRACT

To concentrate a material by separating it from a diluting medium, the combination of the material and medium is placed in one of two wells in the bottom of a plastic sample concentrator cell, with each well being closed at its bottom end by a different cellophane membrane in contact with a buffer solution in a different one of two buffer compartments. A buffer solution also connects the combination of material and medium in one well and the cellophane bottom of the other well within the sample concentration cell through a recess in the bottom of the sample concentration cell. A potential is applied across the two buffer compartments to cause the material to migrate by electrophoresis from the medium in one well, through the buffer in the sample concentrating cell and into the other well, where it is concentrated against the cellophane membrane for easy removal by pipetting.

9 Claims, 14 Drawing Figures

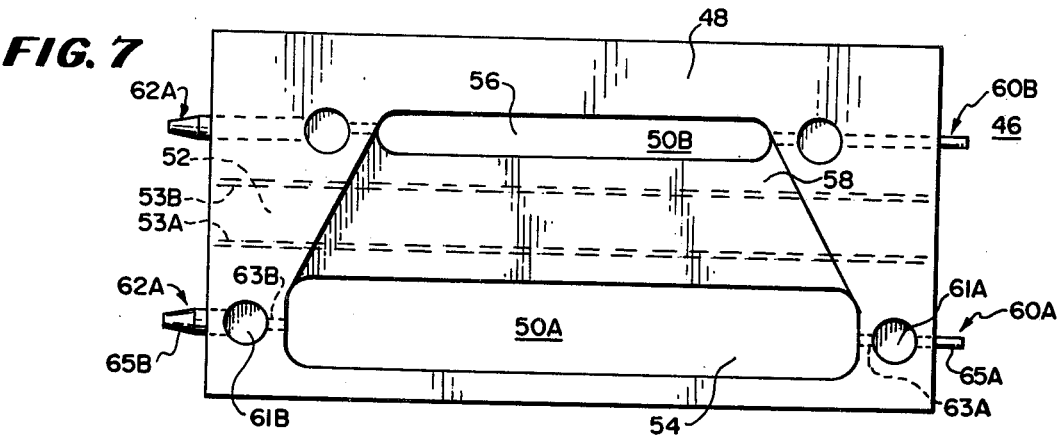
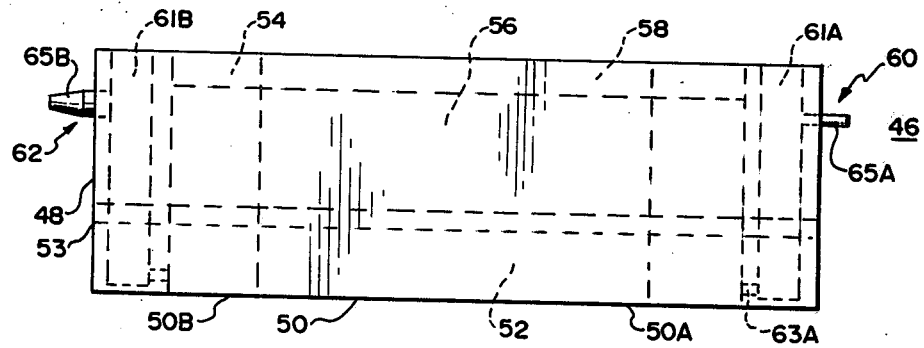
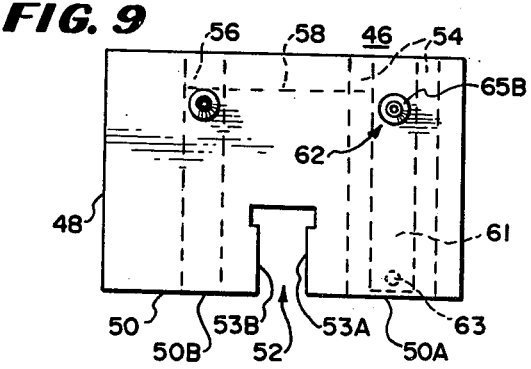
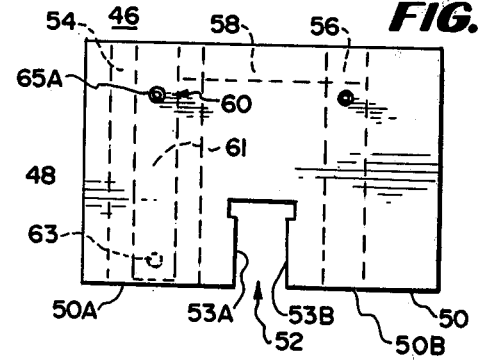
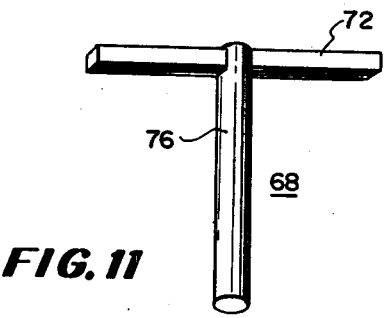
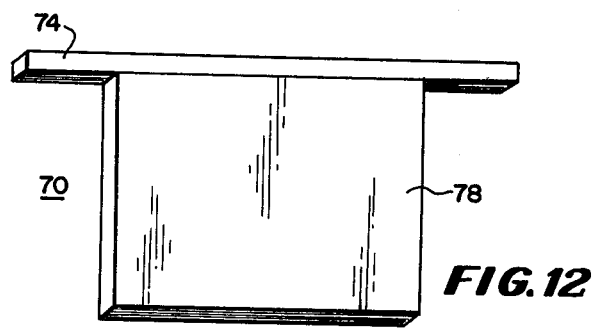

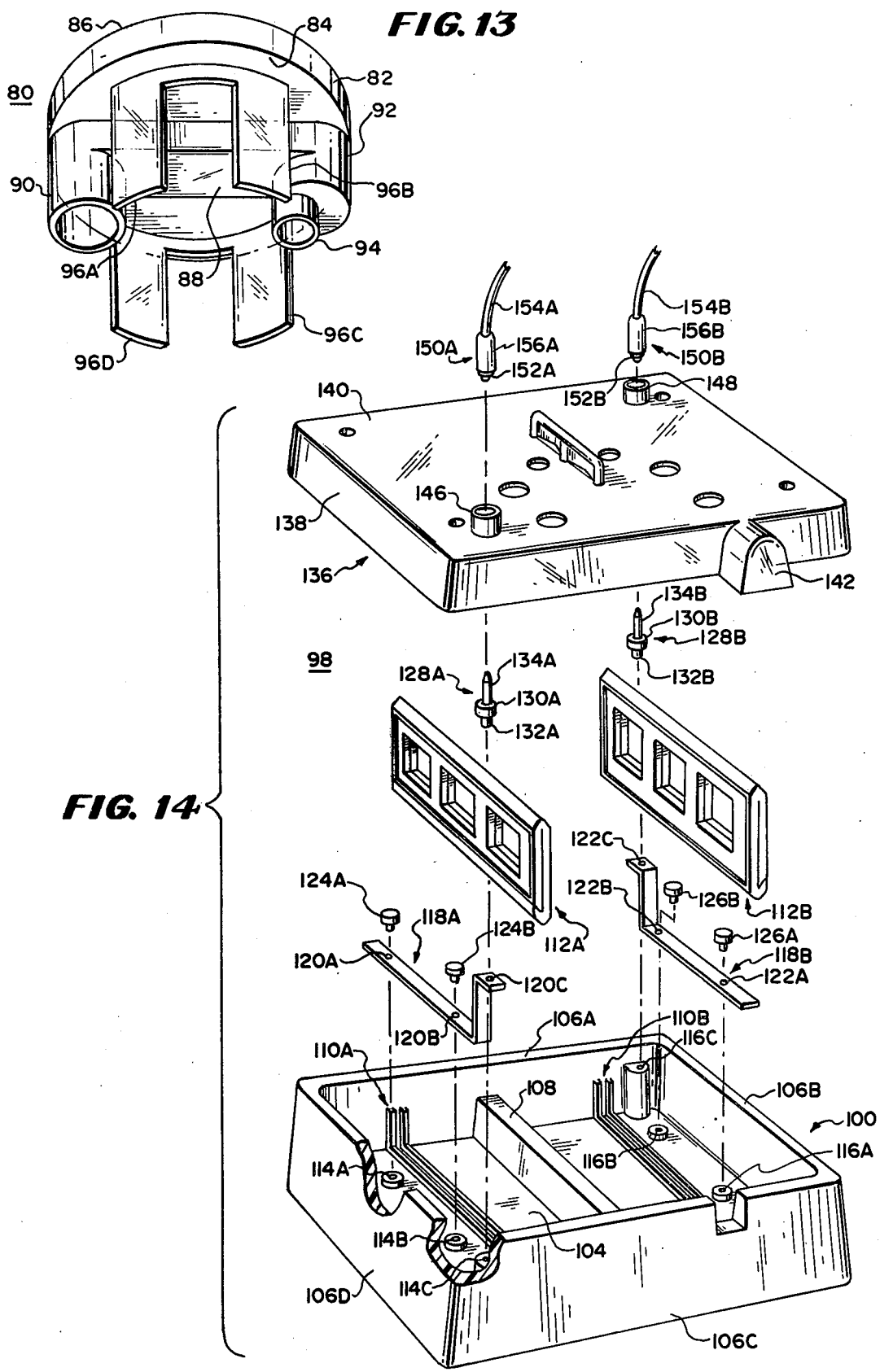

SAMPLE CONCENTRATOR

This invention relates to methods and apparatuses for concentrating samples.

Materials which have been separated one from the other in chromatographic or other processes are often combined with a medium used in the separation. For example, proteins separated by certain density-gradient centrifugation processes are in a sucrose solution after being collected and proteins separated by certain electrophoresis processes are in a polyacrylamide gel after being separated. The materials are separated from the diluting medium and concentrated before being analyzed or used. Moreover, it is, under some circumstances, desirable to concentrate samples before separating the molecular species of the samples by chromatography.

In the prior art, these materials are generally separated and concentrated by dialysis and evaporation if they are in a liquid medium and by elution followed by dialysis and evaporation if they are in a gel medium. These prior art methods and apparatuses for separating the desired materials from a combination of the materials and a medium have the disadvantage of being relatively slow, requiring twelve or more hours under some circumstances.

Attempts have been made in the prior art to reduce the time required for concentrating some dilute proteins by applying an electric field across the dilute protein to electrophores the protein from a first side of a filter paper separator, which serves as an anticonvection element to a second side where it is collected in concentrated form. A prior art method using this principle is disclosed in U.S. Pat. No. 3,079,318. This prior art method has the disadvantages of not providing sufficient separation, being relatively slow and losing some of the proteins in the filter paper.

Accordingly, it is an object of the invention to provide a novel method for concentrating samples by separating them from a diluting medium.

It is a further object of the invention to provide a novel apparatus for concentrating samples.

It is a still further object of the invention to provide a relatively rapid method for concentrating samples by electrophoresis.

It is a still further object of the invention to provide an apparatus capable of concentrating samples in a relatively short time.

It is a still further object of the invention to separate and concentrate a sample from a large volume of unwanted material in a continuous flow process.

In accordance with the above and further objects of the invention, a plastic sample concentration cell includes two wells in its bottom surface, each of which is closed by a porous membrane of a material such as cellophane (reconstituted cellulose). One of the wells is larger than the other and the two wells are connected by a recess in the inside bottom wall of the sample concentration cell.

In one embodiment, the sample concentration cells are adapted to be mounted to an electrophoretic cell having four side-by-side buffer compartments, with one of the wells contacting the buffer in a first inner buffer compartment and the other well contacting the buffer in a second outer buffer compartment of the electrophoretic cell, the first and second buffer compartments being insulated from each other except through the sample concentration cells and having a first outer buffer compartment adjacent to one side of the first inner buffer compartment and a second outer buffer compartment adjacent to one side of the second inner buffer compartment. The path between the cells is advantageously cooled such as by tubes carrying a fluidic coolant.

In one mode of operation, the sample is pipetted into the larger of the wells and the bottom of the recess in the sample concentrating cell is covered with a buffer solution to permit an electrical current to flow from the buffer in one of the buffer compartments through one of the porous membranes, the well containing the sample, the buffer solution in the recess in the sample concentrating cell, the porous membrane of the other well and into the buffer solution in the second buffer compartment. In another mode of operation, the entire sample concentrating cell is filled by the sample solution and in still another mode of operation, the sample solution flows continuously through the cell and the concentrate is removed.

In each mode of operation, a potential is applied across the buffer compartments, causing the material in the well containing the sample to migrate by electrophoresis within the sample concentrating cell to the other well, where it is forced against the cellophane membrane at the bottom of the well, while the diluting medium remains in the first well. Care is taken to avoid the excessive dilution of the sample by the buffer except for the movement of the electrophoresed material. Generally, this dilution may be avoided by selecting a buffer having a specific gravity that is not substantially greater than that of the sample.

The starting material may be any material that includes: (1) relatively large molecular species which migrates in the presence of an electric field; (2) smaller ions which can pass through the porous membrane; and (3) materials which do not migrate with any substantial velocity in the presence of the electric field. The wells serve to separate the starting material from the concentrated material but other structures may be utilized for the same purpose, and, for some combinations, no particular structure is necessary, such as the case where material is moved from one gel into another gel at a different location. In one embodiment, the larger well is elongated and the dilute sample is continuously inserted in one side in a heavy solution beneath the surface of the buffer and removed from the other side during operation to provide a continuous flow of dilute sample for concentration in the smaller well. Moreover, the concentrate may also be continuously removed.

The methods and apparatuses of this invention have the advantages of operating relatively rapidly and being capable of moving a material from one medium into a protective medium when this is desired. Moreover, in one embodiment, a continuous flow of a dilute sample may be concentrated.

The above noted and other features of the invention will be better understood from the following detailed description when considered with reference to the accompanying drawings in which:

FIG. 7 is a plan view of another sample concentrating cell usable in the sample concentrator of FIG. 1;

FIG. 8 is a side elevational view of the sample concentrating cell of FIG. 7;

FIG. 9 is a back elevational view of the sample concentrating cell of FIG. 7;

FIG. 10 is a front elevational view of the sample concentrating cell of FIG. 7;

FIG. 11 is a perspective view of a cylindrical volume-reducing insert useful in the embodiment of FIGS. 4, 5 and 6;

FIG. 12 is a perspective view of a parallelepiped-shaped volume-reducing insert useful in the embodiment of FIGS. 7, 8, 9 and 10;

FIG. 13 is a perspective view of another embodiment of sample concentrating cell; and FIG. 14 is an exploded perspective view of another embodiment of a portion of a sample concentrator.

Figure 1:
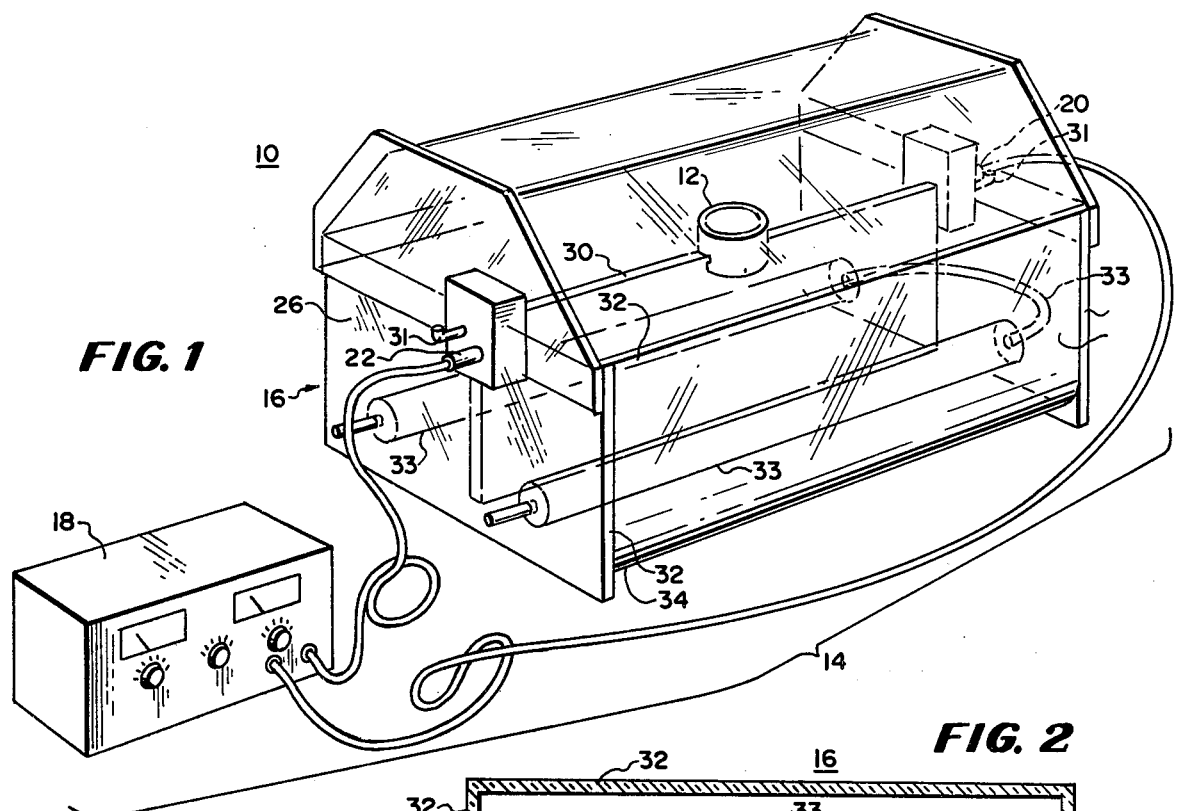
FIG. 1 is a simplified perspective view of a sample concentrator in accordance with an embodiment of the invention.
Figure 2:
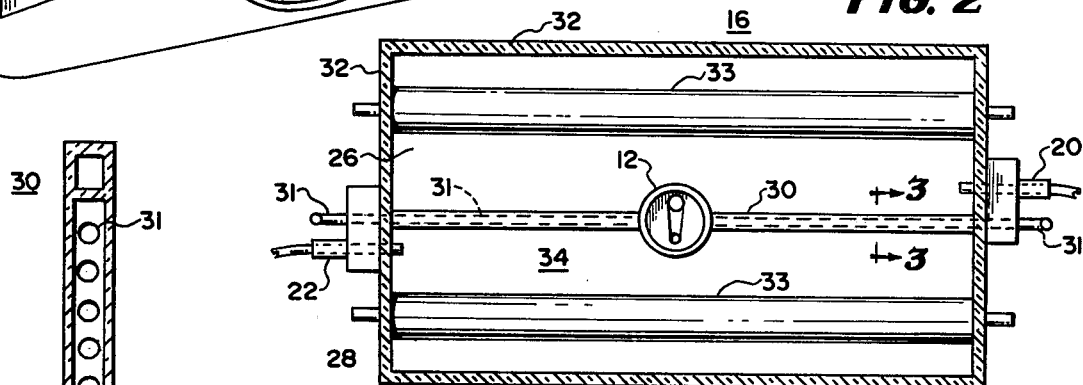
FIG. 2 is a plan view of the embodiment of FIG. 1.

In FIGS. 1 and 2 there is shown an early embodiment of a sample concentrator 10 having a sample concentrating cell 12 and an electrophoretic section 14, with the electrophoretic section 14 including an electrophoretic cell 16 and an electrical power supply 18. The sample concentrating cell 12 rests within the electrophoretic cell 16, having its bottom side in contact therewith and the electrical power supply 18 is electrically connected to the sample concentrating cell 12 through the electrophoretic cell 16.

To provide an electrical potential to the electrophoretic cell 16, the electrical power supply 18 of the electrophoretic section 14 includes first and second electrodes 20 and 22, which are insertable into the electrophoretic cell 16, with the electrode 20 being electrically connected to the positive output terminal of the DC power supply 18 and the electrode 22 being electrically connected to the negative output terminal of the DC power supply 18, by electrical cords. The power supply 18 and the electrodes 20 and 22 are of any suitable type used for electrophoresis, many brands of which are sold and which commonly provide potentials of up to approximately 2000 volts DC.

To provide the electrical potential to the sample concentrating cells 12 in the embodiment of FIG. 1, the electrophoretic cell 16 includes plastic wall portions forming two buffer compartments 26 and 28 cooled by water coils 33 with the two compartments 26 and 28 being separated from each other by a vertical, elongated, separating wall 30 which extends the length of the buffer compartments 26 and 28 within four enclosing side walls 32 and a bottom 34 of the electrophoretic cell 16. The walls 30 and 32 and the bottom 34 of the electrophoretic cell 16 are of any suitable plastic such as polycarbonate suitable for containing a buffer solution.

The separating wall 30 may be cored for cooling and is dimensioned with a width that tightly receives the sample concentration cell 12.

In another embodiment described hereinafter, two outer compartments are formed between the walls 32 and the separating wall 30 in the compartments 26 and 28 by two semipermiable membranes which extend the length of the buffer compartments parallel to the separating wall 30, with one membrane being located between the separating wall 30 and one side wall portion and the other membrane being located between the separating wall 30 and an opposite side wall portion. The outer buffer compartments contain buffer solution having a higher concentration than the buffer solution in the inner compartments. Each of the electrodes 20 and 22 make electrical contact with the buffer solution within a different one of the outer buffer compartments.

Figure 3:
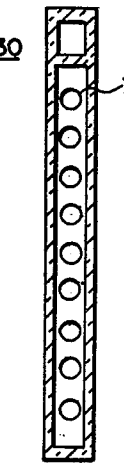
FIG. 3 is a sectional view through lines 3—3 of FIG. 2.

As best shown in FIGS. 2 and 3, the separating wall 30 includes within it a chamber having tubing 31 which extends through the walls 32 where it may be connected to a source of coolant to cool the upper end of the separating wall 30 and the concentrating cell 12 that rests upon it.

While specific separate electrophoretic and sample concentrating cells 12 are shown in FIGS. 1 and 2, other configurations of sample concentration are possible such as configurations having integrally-formed sample concentrating and electrophoretic cells. Generally, the electrophoretic cell should have electrodes or structure to receive electrodes which apply a potential difference across portions of the sample concentrating cells, and advantageously have compartments for a buffer solution which is useful in providing a flow of ions in the field caused by the electric potential.

Figure 4:
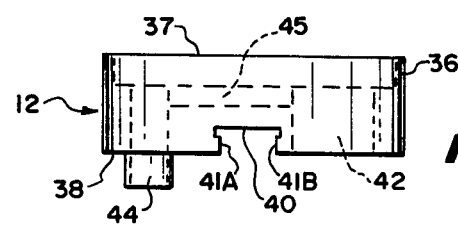
FIG. 4 is an elevational view of a sample concentrating cell used in the sample concentrator of FIG. 1.

In FIG. 4, there is shown one embodiment of sample concentrating cell 12 having an outer vertical cylindrical wall 36 and a bottom wall 38 forming a compartment 37 (FIGS. 4 and 6) suitable for holding fluids.

As shown in FIG. 4, the bottom wall 38 includes a groove 40 having a width substantially the same size as the width of the separating wall 30 so that the sample concentrating cells 12 rest upon the separating wall 30 (FIG. 2) with the top edge of the wall 30 witting within the groove 40 to hold each sample cell in place and properly aligned.

Two side legs 41A and 41B project from the walls of the groove 40 near their bottom and spaced from the top wall of the groove to prevent buffer solution from moving up the separating wall 30 to electrically short the two buffer compartments 26 and 28. The projections space the walls of the groove 40 from the sides of the separating wall 30 to avoid capillary action. Of course, projections on the wall 30 or channels or other devices may be used for this purpose as well.

Although only one cell is shown resting on the separating wall 30 in FIGS. 1 and 2, it is obvious that different numbers of such cells may rest on the wall with portions of the cells extending to either side of the wall where they are in intimate contact with the buffer solution in the buffer compartments 26 and 28, the separating wall 30 advantageously being lower than the outer wall 32 for this purpose. When more than one cell is used, care must be taken to control the parallel electrical paths formed thereby to achieve the desired results.

To receive a potential applied to a buffer solution within the buffer compartments 26 and 28, the bottom wall 38 (FIGS. 4 and 6) of the sample concentrating cell 12 includes two apertures 42 and 44 connected by a recess 45, each aperture being positioned on a different side of the groove 40. As best shown in FIG. 4, the aperture 44 extends downwardly through a cylindrical projection from the bottom wall 38 to provide a longer aperture. The apertures are circular in cross-section and closed at the bottom surface by a porous membrane such as a cellophane membrane to form in the inner bottom wall of the separating cells 12 (FIG. 6) cylindrical wells extending downwardly into the bottom wall 38 and being closed at their bottom surfaces by membranes where engagement is made with buffer in the buffer compartments 26 and 28.

The well 42 has a larger cylindrical bottom area than the well 44 and is normally positioned over one of the buffer compartments 26 and 28, receiving the electrode 20 that has a positive potential applied thereto. The smaller well 44 is positioned over the other buffer compartment which receives the electrode 22 having a negative potential applied thereto. The large well 42 is the sample well or starting mixture well and the smaller well 44 is the receiving well or the concentrate well. For some applications, the larger well 42 may be positioned over the compartment receiving a negative potential and the well 44 over the compartment receiving a positive potential.

Figure 5:
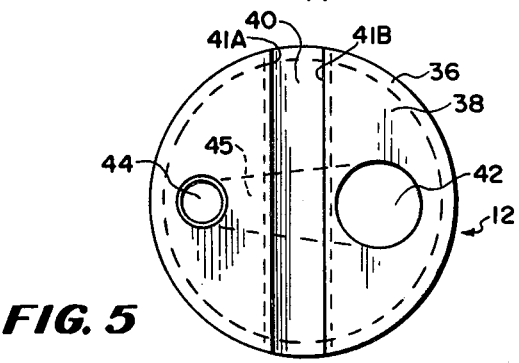
FIG. 5 is a bottom view of the sample concentrating cell shown in FIG. 4.
Figure 6:
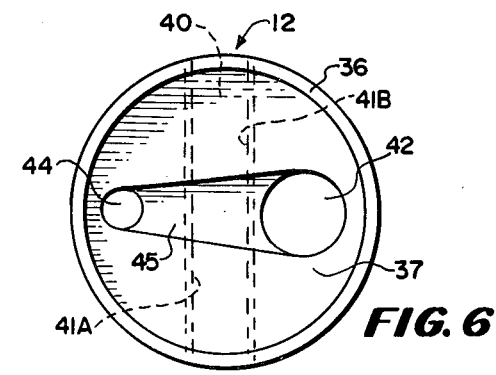
FIG. 6 is a plan view of the sample concentrating cell shown in FIG. 4.

While the sample concentrating cells 12 shown in FIGS. 4-6 are generally cup shaped, they need not be; but only need to include a path which permits ion flow between two other sections one of which contains a concentrate of a first material having a relatively high migration rate in the presence of an electrical field and which cannot readily pass through the semipermeable membrane closing the well 44 and the other of which contains the starting mixture containing the first material diluted with a second material which second material either has a lower rate of or no migration in the presence of the electric field so that the concentrate is movable from the starting or sample section to the receiving or concentrate section or can pass through the semipermeable membrane slowing the well 44. To separate some materials, for example, separate sample and concentrate wells are unnecessary and a flat bottom surface or single trench is sufficient such as when separating the concentrate from a gel since the gel remains separated from the concentrate portion even though it rests above or at the same level of the sample separating cell as the concentrate.

In FIGS. 7-10, there is shown a sample concentration cell 46 having the general shape of an open top right regular parallelepiped with upstanding vertical walls 48 and a bottom wall 50. As best shown in FIGS. 8 and 9, the bottom wall 50 on the bottom outside thereof includes the rectangular recess 52 which is substantially of the same shape and size as the top of the separating wall 30 (FIG. 2) so as to permit the sample concentrating cell 46 to be mounted thereto. Within the rectangular recess 52 are inwardly extending legs 53 similar to the projections 41A and 41B in FIG. 4 to space the walls of the recess 52 sufficiently far from the sides of the separating wall 30 to avoid capillary movement of buffer up the separating wall 30 from the compartments 26 and 28 to electrically short these compartments.

In the bottom wall on one side of the rectangular groove 52 is a first aperture or well 54, shaped as a right regular parallelepiped and on the opposite side is a smaller aperture or well 56, having the same general shape with each of the apertures 54 and 56 being sealed to the bottom wall 50 by a different cellophane membrane or different portions of the same membrane to form a porous contact between the apertures 54 and 56 and a buffer at 50A and 50b respectively. When the sample concentrating cell 46 is mounted in intimate contact with the buffer in respective ones of the buffer chambers 26A and 28A, the apertures 54 and 56 with their respective membrane bottoms form the sample well 54 and concentrate well 56 respectively. The sample well 54 is connected to the concentrate well by a connecting recess 58 in the top surface of the bottom wall 50 to permit the flow of the material being separated between the sample cell and the concentrate cell and to receive a covering buffer solution to facilitate this flow.

To permit a large volume of dilute sample to be concentrated, the sample concentrator 46 includes an inlet 60A and an outlet 62A, ecch being within the wall 48 on a different side of the sample well 54. The inlet 60 includes a downwardly-extending cylindrical recess 61A communicating with a first end of the sample well 54 near its bottom through a tube 63A and with an inlet tube 65A at a height above the top of the connecting recess 58 and the outlet 62 includes a downwardly-extending cylindrical recess 61B communicating with the second end of the sample well 54 near its bottom through a tube 63B and with an outlet spout 65B at a height above the top of the connecting recess 58.

These connections are arranged to permit the continuous flow of a dilute sample through the sample well 54 at a level below the buffer therein for continual removal of the material to be concentrated to the concentrate well 56, with the spout 65B being sufficiently large to avoid siphoning action. Preferably the buffer has a lower density than the sample so the sample flows across the top of the membrane with the buffer floating on top of the sample.

Similar connections including an inlet 60B, an outlet 62B, recesses 61C and 61D, tubes 63C and 63D and inlet tubes 65C and 65D provide for continuous flow of concentrate through the concentrate well. This is possible because the concentrate is more dense than the buffer and flows along the bottom of the concentrate well.

Generally, the semiporous membranes that close the sample and concentrate wells extend along a portion of the bottom surfaces of the concentration cells on each side of the groove 40 or 52 to cover the bottom of the wells 42, 44, 56 and 58 for convenient sealing and fabrication of the sample and concentration wells. In one embodiment, the semiporous membranes are held in place by acrylic rings that extend part way into the grooves 40 and 52 and surround the walls of the sample concentrate cells, holding the edge of the membrane between them and the walls. In this embodiment the rings also space the walls of the cell from the separating wall 30 to prevent capillary action. The remainder of the sample concentration cells 12 and 46 are of any suitable plastic such as polycarbonate or acrylic.

In the embodiment of FIGS. 7-10, structure is shown to permit continuous in line operation to concentrate large amounts of dilute sample. Of course, this type of structure can also be used in other embodiments of sample concentration cells such as the embodiment of FIGS. 4-6.

In FIGS. 11 and 12, there are shown two different concentrate-well-volume reducers 68 and 70, each having a different one of the elongated handles 72 and 74 respectively and a different one of the well inserts 76 and 78 respectively. These volume reducers are in different sizes to fit with concentrate wells, with the reducer 68 fitting within a cylindrical well and the reducer 70 within wells have a rectangular cross-section to reduce the amount of buffer above the concentrate in the well for ease in removing the concentrate.

Before operating the sample concentrator 10, a suitable number of sample concentrating cells 12 or 46 are positioned on the separating wall 30 with the sample well 42 or 54 being positioned over the buffer compartment 26 and the concentrate wells 44 or 56 being positioned over the buffer compartment 28. The separating wall 30 is received by the grooves 40 or 52 of the sample concentrating cells 12 or 46. If the concentrate is expected to be substantially lower in volume than the volume of the concentrate well, a reducer 68 or 70 is inserted into the concentrate well to reduce the volume of the buffer in the well.

With the cells mounted to the separating wall 30, buffer is applied to the buffer compartments 26 and 28 and the electrodes 20 and 22 are inserted into the buffer, with the buffer extending up to the top of the separating wall 30 but not over the wall so that the compartments 26 and 28 are electrically insulated from each other except through the sample cells 12 or 46 which extend into the buffer solutions. The electrode 20 is electrically normally connected to the positive output terminal and the electrode 22 is normally electrically connected to the negative terminal of the power supply 18. A coolant is circulated through the tube 31 of the separating wall 30 so that a relatively large current may be used for rapid separation of the concentrate from the sample without overheating the concentrate. The temperature of the coolant is selected in accordance with the need to maintain a low temperature.

In the embodiment of FIGS. 4–6, the sample is inserted into the sample wells 42 of the sample concentrating cells 12 and a buffer solution is applied over the sample wells 42, concentrate wells 44 and recesses 45 to connect the sample wells 42 to the concentrate wells 44 through the recesses 45. In the embodiment of FIGS. 7–10, connections are made to the inlet tube 65A and outlet tube 65B to apply a continuous flow of sample therethrough, with a buffer solution being placed over the sample compartments 54, the recesses 58 and concentrate compartments 56 to form an electrical connection therebetween.

With this arrangement, a positive potential normally is applied to the electrode 20 and normally a negative potential to the electrode 22 to provide a path for electrical current from the electrode 20 to the electrode 22. Generally the sample concentrating cells are arranged so that the current flows through the buffer solution in the buffer compartment 26, through the cellophane bottom of the concentrate well, through the buffer solution within the sample cups, downward through the cellophane bottom of the sample well, into the buffer solution within the compartment 28 and finally to the electrode 22. This causes the migration of negative ions from the sample well to the concentrate well and positive ions to the sample well with small ions passing through the cellophane bottom of the concentrate well and into the buffer solution in the buffer compartments while the concentrate to be separated is held by the cellophane membrane to be gathered in the concentrate well and the substance which does not migrate remaining in the sample well. This arrangement of concentrating cells is used with negatively charged proteins and a reverse arrangement would be used to concentrate positively charged substances.

The connecting passageways (45 in FIGS. 4, 5 and 6 and 58 in FIGS. 7–10) restrict the flow of concentrate to an area having a relatively uniform field and ion flow to avoid its being deposited at a location between the sample well and concentrate well. To aid in confining the ion flow to the area of strong uniform field strength, the recesses 45 and 58 conform to the sizes of the wells adjacent to their ends and slope uniformly between their ends in the manner of the electric field.

Generally, the concentrate is a protein which is to be separated and is diluted by another material such as a sucrose solution of the type used in density-gradient centrifugation. Of course, other materials such as glycerol may form the base instead of sucrose as well as many other of the usual materials used in chromatography.

Although the preferred embodiment contemplates the removal of proteins from sucrose or the like material and its deposition into a well where it is to be held at the bottom of the well by gravity, other materials may be separated from a gel such as polyacrylamide gel and deposited in another location in the sample concentrating cell or may be moved into another material. Similarly, the concentrate may be moved from one material such as a sucrose of one density and into another material such as a more dense sucrose, glycerol or some other material useful in further preparation of the sample or in analysis of the sample.

When the sample concentrating cell is being used to transfer a sample material from one substance to another, the sample material may or may not be more concentrated in the new substance. For example, the transfer may be the transfer of a protein from sucrose to glycerol and the concentration of the protein in the glycerol may be lower, the same, or higher than it was in the sucrose. Moreover, the sample concentrator may be used to transfer some species of materials through the walls of the separating cell and retain others in the cell.

While the sample concentrating cells 12 or 46 are intended primarily to separate the material that is being studied from the medium that it is in, which medium is present because it was used in the process of separating one molecular species from another or in receiving a separated molecular species from another material for collecting in a commercial sample collector, it may be desirable to move it into another material because it has been found that some proteins have active radicals attached to them which should not be exposed into the atmosphere or which should be protected in one manner or another. By moving the concentrate into a protective substance, further information may be obtained about the nature of the concentrate.

Once the concentrate has been separated from the medium of the starting material, it may be removed by a pipette for further study in any commercial analyzing apparatus or for use as a preparative material. To remove the material, the buffer is pipetted from the recesses of the sample concentrator cell. The volume reducer is removed, leaving only a small amount of buffer in the concentrate well some of which may be removed, after which the concentrate is removed by pipetting.

In FIG. 13, there is shown another embodiment 80 of a sample concentrating cell having an outer vertical cyindrical wall 82 and a bottom wall 84 forming a compartment 86 in a manner similar to the embodiment of FIGS. 4–6. This embodiment includes an upwardly opening groove formed by a trough-shaped recess 88. The sample concentrating cell 80 rests upon the separating wall (31 in FIG. 2, 108 in FIG. 14) with the top edge of the wall 31 being below the recess 88 and thus does not have a recess into which the wall portion fits as do the embodiments of FIGS. 4–10. The recess is omitted to reduce problems with capillary action from the buffer compartments.

To receive the potential difference applied across the buffer solutions, two cylindrical wells 90 and 92 extend downwardly from the trough 88, with the well 90 being slightly longer and with the well 92 including a smaller cylindrical projection 94 extending downwardly to substantially the same length as the well 90, with the well 92 being closed except for communication with the cylindrical projection 94. In the embodiment of FIG. 13, the well 90 serves as the sample well or starting mixture well and the well 92 serves as the receiving well or concentrate well, with the concentrate being moved generally downwardly into the projection 94 which is smaller in diameter so as to have a more concentrated field. The bottoms of the wells are, of course, closed by a porous membrane in the same manner as the embodiment of FIGS. 4–6.

To aid in supporting the sample concentrating cell 80 about a separating wall, four legs 96A–96D extend downwardly from the bottom 84 of the sample concentrating cell, with adjacent legs 96A and 96B being joined by a plastic strip closer to the bottom wall 84 than the bottom of the recess 88 and with the legs 96C and 96D being joined by a corresponding strip.

The legs 96A–96D are thin plastic downwardly extending members which are sections of a cylinder and which have edges aligned with the inner edges of the wells 90 and 92 with the inner edges of the legs 96A and 96D being aligned with the inner edge of the tube 90 and the inner edges of the legs 96B and 96C being aligned with the inner edge of the well 92. With this arrangement, the opposite sides of the separating wall contact the inner edges of the legs 96A and 96D on one side and 96B and 96C on the other side. The legs are spaced to support the cell 80 on the separating wall (30 in FIG. 2 and 108 in FIG. 14) by passing along the sides of the wall.

In FIG. 14, there is shown an exploded perspective view of another embodiment of electrophoretic cell 98 having a buffer compartment section 100 and a cover and electrode section which fits over and closes the buffer compartment section 100.

To provide for buffer compartments, the buffer compartment section 100 is generally parallelepiped in shape having a bottom wall 104, four side walls 106A–106D and an open top, with the four side walls and the bottom wall forming a compartment for holding buffer solutions. To support sample concentrating cells, a center separating wall 108, shaped as a parallelepiped extends upwardly from the bottom wall 104 to a height less than the side walls 106A and 106C which it intersects to divide the open portion of the buffer compartment 102 into two sections, thus permitting the sample concentrating cells to rest on top of the separating wall 108 in a manner analogous to the manner in which the separating cells rest on the separating wall 31. The separating wall 108 is hollow and may support a plurality of cooling coils.

To separate each of the two sections of the buffer compartment section 100 on each side of the separating wall 108 into two buffer compartments, there is formed on the bottom wall 104 and side walls 106A and 106C on a first side of the separating wall 108, mounting tracks 110A and on the other side of the separating wall 108, mounting tracks 110B, with the mounting tracks 110A and 110B each including a recess in the bottom wall 104 and the side walls 106A and 106C bordered on each side by upwardly extending ridges.

The recesses and ridges forming the mounting tracks 110A are shaped to receive a first separating membrance 112A and the recesses and ridges forming the separating tracks 110B are shaped to receive a second separating membrane 112B and for this purpose extend parallel to the separating wall 108. The mounting tracks and separating membranes separate two outer high concentrate compartments from two inner lower concentrate compartments.

To mount electrodes within the buffer solutions in the outer high concentrate compartments, the compartment formed between the separating membrane 112A and the side wall 106D between walls 106A and 106C includes in the bottom wall 104 two cylindrical elevated bosses 114A and 114B and a large upwardly extending boss 114C which extends above the heighth of the separating wall 108. Similarly, in the compartment formed by the separating membrane 112B and the side wall 106B between portions of the walls 106A and 106C, the bottom wall 104 includes two upwardly extending bosses 116A and 116B and a larger upstranding boss 116C which extends above the heighth of the separating wall 108.

To provide electrical contact with the buffer solution in the outer compartment, a first electrode 118A is mounted to the bosses 114A–114C and a second electrode 118B is mounted to the bosses 116A–116C. The first electrode 118A and the second electrode 118B are each formed as thin metal strips shaped as L's, each with a long bottom section and an upstanding arm with an outwardly extending ear on it. The long bottom section of the electrode 118A includes first and second apertures 120A and 120B which are aligned with central apertures in the bosses 114A and 114B and the outwardly extending ear has a third aperture 120C which is aligned with the aperture in the larger boss 114C.

The electrode 118A is designed to fit within the outer compartment with the metal strip extending parallel to the separating wall 112A and the retaining apertures 120A–120C fitting over apertures in the bosses 114A–114C. Similarly, the electrode 118B includes three apertures 122A, 122B, and 122C each adapted to be aligned with a different one of the central apertures in the bosses 116A, 116B, and 116C for mounting in a manner similar to electrode 118A.

To hold the electrodes 118A and 118B in place (1) first and second retainers 124A and 124B each have a head portion larger than the apertures 120A and 120B and a shank which fits through the apertures 120A and 120B and frictionally engages the apertures in the centers of the bosses 114A and 114B; and (2) retainers 126A and 126B have heads larger than the apertures 122A and 122B and shanks that fit through apertures 122A and 122B and frictionally engage the center apertures in the cylindrical bosses 116A and 116B. The electrodes 118A and 118B are positioned against the bottom 104 of the base buffer compartment and the retainers 124A, 124B, 126A and 126B are positioned with their shanks passing through the apertures in the corresponding holes in the bosses to hold the electrodes 118A and 118B in place.

To provide electrical connection to the electrodes 118A and 118B from outside of the buffer section 100, first and second electrical contacts 128A and 128B each include a corresponding one of the central cylindrical sections 130A and 130B separating bottom cylindrical sections 132A and 132B and top pin shaped portions 134A and 134B respectively. The bottom cylindrical sections 132A and 132B are of such a size as to fit respectively through the apertures 120C and 122C and fit tightly within the central apertures in the bosses 114c and 116C. The central cylindrical sections 130A and 130B are larger than the apertures 120C and 122C so as to fit on top of the electrodes 118A and 118B when mounted in position and the top pin shaped portions 134A and 134B make electrical connection outside of the buffer solution to conductors as will be described hereinafter. The bottom cylindrical portions 132A and 132B have central openings in their bottom surface which permit easy swedging of the metal around the bottom of the upwardly extending bosses 114A and 116A to hold the electrodes in place.

The separators 112A and 112B are plastic members of white polypropylene which are folded over and include windows of a semi-permeable material that allow electrical current to pass between the compartments but maintain the high concentration compartment separate from the lower concentration compartment. The folded over sections include hook-like members in their ends which fit against the upstanding members in the tracks 110A and 110B respectively to hold the separators in place.

To cover the sample concentrator when it is in use, a plastic cover 136 is shaped as a parallelepiped with downwardly extending walls 138 which fit around the walls of the base buffer section 100 and a plastic top portion 140. To provide an outlet for fluids which may be useful for some applications, a hooded opening 142 is provided which fits within a notch in the wall 106 of the buffer section 100. To permit the injection of samples into sample cells and the removal of concentrate, there are a plurality of openings 144 in the top of the cover.

To permit electrical connection through the cover 136, the cover 136 includes cylindrical members 146 and 148, each of which are hollow cylinders passing through the top of the cover 136 with a bottom partly closed to a form a small central aperture and an open top. The small cylindrical apertures in the bottoms of the cylinders 146 and 148 are aligned with the top pin-shaped connectors 134A and 134B respectively when the cover 136 is properly positioned on the base buffer section 100 so that the pins 134A and 134B extend upwardly therein to make electrical connection outside of the cover.

To connect the pins 134A and 134B to a power supply, first and second female connectors 150A and 150B each have a different hollow conductive connecting member 152A and 152B with a recess adapted to fit tightly about a corresponding one of the pins 134A and 134B. The conductors 152A and 152B are connected to cables 154A and 154B respectively and are mounted within an insulating member 156A and 156B. The insulating member 156A fits comformably within the cylinder 146 and the insulating member 156B fits comformably within the cylinder 148 so that the conductors 150A and 150B may be inserted into the cylinders 146 and 148 to make electrical connection to the electrodes 118A and 118B in the power supply.

As can be understood from the above description, the methods and apparatuses of this invention have the advantages of being able to quickly concentrate dilute material with high recovery.

While a preferred embodiment has been described in some detail, many modifications and variations in the preferred embodiment are possible in the light of the above teachings. Therefore, it is to be understood that, within the scope of the appended claims, the invention may be practiced other than as specifically described.

What is claimed is:

1. A method of removing at least one molecular species from a sample, comprising the steps of:

moving the sample to a first location;
transporting said one molecular species to a second location spaced from the first location on a first side of a membrane having pores sufficiently small to hold said molecular species;
said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the sample to a position against the first side of the membrane;
removing at least a portion of the first molecular species from the first side of the membrane;
the step of transporting said one molecular species to a second location including the step of transporting said one molecular species to a second location spaced from the first location on a first side of a first membrane;
said step of moving the sample to a first location including the step of placing said sample on a first side of a second membrane; and
the step of establishing an electrical field between the first location and a third location including the step of establishing an electrical potential between the second side of the second membrane and the second side of the first membrane.

2. A method according to claim 1 in which the step of establishing a potential between the first and third locations further includes the step of establishing a potential difference between a first buffer solution in intimate contact with the second side of the first membrane and a second buffer solution in intimate contact with the second side of the second membrane, said first and second solutions being insulated from each other.

3. A method according to claim 2 further including the step of placing a protective material against the first side of the first membrane, whereby said one molecular species is moved into said protective material.

4. A method according to claim 3 further including the step of continuously passing different portions of said sample through said first location, whereby said one molecular species is continuously moved from a flowing sample.

5. A method of removing at least one molecular species from a sample, comprising the steps of:

moving the sample to a first location;
transporting said one molecular species to a second location spaced from the first location on a first side of a membrane having pores sufficiently small to hold said molecular species;
said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the sample to a position against the first side of the membrane;
removing at least a portion of the first molecular species from the first side of the membrane;

said step of moving the sample to a first location including the step of placing said sample on a first side of a second membrane; and the step of establishing an electrical field between the first location and the third location including the step of establishing an electrical potential between the second side of the second membrane and the second side of the first-mentioned membrane.

6. A method according to claim 5 in which the step of establishing a potential between the second and third locations further includes the step of establishing a potential difference between a first buffer solution in intimate contact between the second side of the first membrane and a second buffer solution in intimate contact with the second side of the second membrane, said first and second solutions being insulated from each other.

7. A method according to claim 6 further including the step of placing a protective material against the first side of the first-mentioned membrane, whereby said one molecular species is moved into said protective material.

8. A method of removing at least one molecular species from a sample, comprising the steps of:

moving the sample to a first location;

transporting said one molecular species to a second location spaced from the first location on a first side of a membrane having pores sufficiently small to hold said molecular species;

said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the sample to a position against the first side of the membrane;

removing at least a portion of the first molecular species from the first side of the membrane; and placing a protective material against the first side of the first-mentioned membrane, whereby said one molecular species is moved into said protective material.

9. A method according to claim 8 further including the step of removing at least a portion of the first molecular species from the first side of the first-mentioned membrane.

* * * * *

UNITED STATES PATENT AND TRADEMARK OFFICE
CERTIFICATE OF CORRECTION

PATENT NO. : 4,159,933
DATED : July 3, 1979
INVENTOR(S) : William B. Allington, et al It is certified that error appears in the above-identified patent and that said Letters Patent are hereby corrected as shown below:

Column 1, line 30, change the word "electrophores" to "electrophorus".
Column 3, line 64, change the word "semipermiable" to "semipermeable".
Column 4, line 33, change the word "witting" to "sitting".
Column 5, line 1, change "with buffer" to "with the buffer".
Column 5, line 61, change "50b" to "50B".
Column 6, line 7, change the word "ecch" to "each".
Column 6, line 36, change the word "bottom" to "bottoms".
Column 6, line 61, change "have" to "having".
Column 8, line 55, change the word "cyindrical" to "cylindrical".
Column 8, line 60, change "31" to "30".
Column 10, line 17, change the word "upstranding" to "upstanding".
Column 10, line 42, after the word "place", place a colon.

Signed and Sealed this

Eleventh Day of December 1979

[SEAL]

Attest:

SIDNEY A. DIAMOND

Attesting Officer

Commissioner of Patents and Trademarks

っっ# REEXAMINATION CERTIFICATE (1694th)

United States Patent [19]

Allington, deceased et al.

[11] B1 4,159,933

[45] Certificate Issued  May 12, 1992

[54] SAMPLE CONCENTRATOR

[75] Inventors: William B. Allington, deceased, late of Lincoln, Nebr., by Richard T. Emery, executor; James W. Nelson, Lincoln, Nebr.; Arthur L. Cordry, Lincoln, Nebr.; Gail A. McCullough, Lincoln, Nebr.; Don E. Mitchell, Lincoln, Nebr.

[73] Assignee: Instrumentation Specialties Co.

Reexamination Request:
No. 90/001,863, Oct. 13, 1989

Reexamination Certificate for:
Patent No.: 4,159,933
Issued: Jul. 3, 1979
Appl. No.: 781,176
Filed: Mar. 25, 1977

Certificate of Correction issued Dec. 11, 1979.

[51] Int. Cl.$^5$ .................... G01N 27/40; G01N 27/26; G01N 27/28
[52] U.S. Cl. ................... 204/182.3; 204/180.1; 204/299 R; 204/182.8; 436/177; 436/516
[58] Field of Search ............... 204/299 R, 301, 180.1, 204/182.8, 182.3, 182.6

[56] References Cited

U.S. PATENT DOCUMENTS

| | | |
|---|---|---|
| 2,758,966 | 8/1956 | Raymond . |
| 2,878,178 | 3/1959 | Bier ........................ 204/180 |
| 3,047,489 | 7/1962 | Raymond . |
| 3,079,318 | 2/1963 | Bier . |
| 3,129,158 | 4/1964 | Raymond et al. . |
| 3,208,929 | 9/1965 | Raymond et al. . |
| 3,255,100 | 6/1966 | Raymond ........................ 204/180 |
| 3,359,194 | 12/1967 | Kollsman . |
| 3,374,166 | 3/1968 | Raymond . |
| 3,392,100 | 7/1968 | Kollsman . |
| 3,440,159 | 4/1969 | McRae et al. ........................ 204/180 |
| 3,470,080 | 9/1969 | Raymond et al. . |
| 3,523,879 | 8/1970 | Cortes . |

(List continued on next page.)

FOREIGN PATENT DOCUMENTS

| | | |
|---|---|---|
| 1254346 | 11/1971 | United Kingdom . |
| 1295771 | 11/1972 | United Kingdom . |
| 1338543 | 11/1983 | United Kingdom . |

OTHER PUBLICATIONS

Karsnas & Roos "Two Methods for Electrophoretic Elution of Proteins for Polyacrylamide Gels" Analytical Biochemistry 77, (1977), pp. 168-175.

Hori "A Method for the Rapid Elution of Proteins from Mashed Gel After Starch Gel Electrophoresis" Journal of Chromatography 94, (1974), pp. 107-112.

(List continued on next page.)

*Primary Examiner*—John F. Niebling

[57] ABSTRACT

To concentrate a material by separating it from a diluting medium, the combination of the material and medium is placed in one of two wells in the bottom of a plastic sample concentrator cell, with each well being closed at its bottom end by a different cellophane membrane in contact with a buffer solution in a different one of two buffer compartments. A buffer solution also connects the combination of material and medium in one well and the cellophane bottom of the other well within the sample concentration cell through a recess in the bottom of the sample concentration cell. A potential is applied across the two buffer compartments to cause the material to migrate by electrophoresis from the medium in one well, through the buffer in the sample concentrating cell and into the other well, where it is concentrated against the cellophane membrane for easy removal by pipetting.

FIG. 1

U.S. PATENT DOCUMENTS

| | | |
|---|---|---|
| 3,579,433 | 5/1971 | Dahlgren . |
| 3,616,454 | 10/1971 | Levy . |
| 3,640,813 | 2/1972 | Nerenberg . |
| 3,674,678 | 7/1972 | Post, Jr. et al. . |
| 3,715,295 | 2/1973 | Tocci . |
| 3,719,580 | 3/1973 | Roberts et al. . |
| 3,720,593 | 3/1973 | Juhos . |
| 3,751,356 | 8/1973 | Takeya et al. . |
| 3,759,773 | 9/1973 | Dwyer et al. . |
| 3,829,375 | 8/1974 | Cawley . |
| 3,888,758 | 6/1975 | Saeed .............................. 204/299 R |
| 3,902,987 | 9/1975 | Cawley . |
| 3,932,263 | 1/1976 | Brefka . |
| 3,951,776 | 4/1976 | Eibl et al. . |
| 3,989,613 | 11/1976 | Gritzner . |
| 4,013,513 | 3/1977 | Lederer . |
| 4,049,534 | 9/1977 | Posner . |
| 4,200,611 | 4/1980 | Gorman, Jr. et al. . |
| 4,608,147 | 8/1986 | Clad . |

OTHER PUBLICATIONS

*Electrophoresis, Theory, Method, and Applications*, Edited by Milan Bier, Academic Press, Inc., 1959.

"Fractionation of Proteins by Electrophoresis-Convection. An Improved Apparatus and its Use in Fractionating Diptheria Antitoxin", by John R. Cann, John G. Kirkwood, Raymond A. Brown and Otto J. Plescia.

"The Fractionation of y-Globulin by Electrophoresis-convection" by John R. Cann, Raymond A. Brown and John G. Kirkwood.

"Electrodialysis and its Applications", by Surendar M. Jain, *American Laboratory*, Oct., 1979.

"The Theory of Electrophoresis-Convection", by John G. Kirkwood, John R. Cann and Raymond A. Brown *Biochemica Et Biophysica Acta*, vol. 5 (1950).

"A Suggestion for a New Method of Fractionation of Proteins by Electrophoresis Convection", by John G. Kirkwood, *Journal of Chemical Physics*, Dec., 1941, vol. 9.

"Electrodecantation of Serum Proteins" by Theodor Kranz and Franz Lappe, *Hoppe-Seyler's z. Physiol. Chem* Bd. 356., S. 1545-1554, Oct., 1975.

"Preparative Methods for Disk Electrophoresis with Special Reference to the Isolation of Pituitary Hormes", by U. J. Lewis and M. O. Clark, *Analytical Biocemistry*, 6, 303-315 (1963).

"Multi-Membrane Electrodecantation and its Application to Isolation and Purification of Proteins and Viruses", by Alfred Polson, *Biochemica Et Biophysica Acta*, vol. 11 (1953).

"The Concentration of Macromolecules by Electrophoresis-Sedimentation", by Israel Posner, *Analytical Biochemistry* 70, 187-194 (1976).

"A New Apparatus for the Recovery of Macromolecules from Polyacrylamide Gel Slabs following Preparative Vertical Gel Electrophoresis", by Israel Posner, *Analytical Biochemistry*, 72, 491-501 (1976).

"Protein Purification by Elution Convection Electrophoresis", by Samuel Raymond, *Science*, vol. 146.

"Simplified Technique for Preparative Disc Electrophoresis", by Dov Sulitzeanu, Marit Slavin and Ezra Yecheskeli, *Analytical Biochemistry*, 21, 57-67 (1967).

*Preparative Electrophoresis and Ionophoresis*, by Harry Svensson.

*Agar Gel Electrophoresis* by R. J. Wieme, Elsevier Publishing Company, pp. 126-128, 1965.

"Enzyme Purification by Electrodecantation", by B. G. Winchester, M. Gaffrey and D. Robinson, *Biochem. J.* (1971) 121, 161-168.

"Mythylated Cellophan Membranes for Possible Use in Multi-Membrane Electrodecantation", by A. Polson, *Experimentia*, vol. 25 (4) 1969.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 5 and 8 are determined to be patentable as amended.

Claims 2-3, 6-7 and 9, dependent on an amended claim, are determined to be patentable.

New claims 10-16 are added and determined to be patentable.

1. A method of *separating, concentrating and* removing at least one molecular species from a sample *as a concentrate*, comprising the steps of:
   placing buffer liquid in first and second buffer compartments of an electrode housing wherein the first and second buffer compartments are separated by a separating wall with at least one of the two buffer compartments being open at the top, whereby a sample concentrating cell may be lowered onto the separating wall;
   lowering the sample concentrating cell onto and mounting it to the separating wall wherein buffer solution in said first buffer compartment wets a first location of said sample concentrating cell and buffer solution in said second buffer compartment wets a second location of said sample concentrating cell;
   moving [the] *said* sample to [a] *said* first location wherein the sample is spaced from said second location in said sample concentrating cell;
   transporting said one molecular species to [a] *said* second location spaced from the first location on a first side of a membrane having pores sufficiently small to hold said *one* molecular species *through a passageway that communicates between the first and second locations;*
   said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the ssample to a position against the first side of the membrane;
   removing at least a portion of the [first] *one* molecular species from the first side of the membrane *in concentrated form from said second location as a concentrate;*
   [the step of transporting said one molecular species to a second location including the step of transporting said one molecular species to a second location spaced from the first location on a first side of a first membrane;]
   said step of moving the sample to a first location including the step of placing said sample on a first side of a second membrane; and
   the step of establishing an electrical field between the first location and a third location including the step of establishing an electrical potential between the second side of the second membrane and the second side of the first membrane.

4. A method [according to claim 3 further including the step of] *of separating, concentrating and removing at least one molecular species from a sample as a concentrate, comprising the steps of:*
   *placing buffer liquid in first and second buffer compartments of an electrode housing wherein the first and second buffer compartments are separated by a separating wall with at least one of the two buffer compartments being open at the top, whereby a sample concentrating cell may be lowered onto the separating wall;*
   *lowering the sample concentrating cell onto and mounting it to the separating wall wherein buffer solution in said first buffer compartment wets a first location of said sample concentrating cell and buffer solution in said second buffer compartment wets a second location of said sample concentrating cell;*
   *moving said sample to said first location wherein the sample is spaced from said second location in said sample concentrating cell;*
   *transporting said one molecular species to said second location spaced from the first location on a first side of a membrane having pores sufficiently small to hold said one molecular species through a passageway that communicates between the first and second locations;*
   *said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the sample to a position against the first side of the membrane;*
   *removing at least a portion of the one molecular species from the first side of the membrane in concentrated form from said second location as a concentrate;*
   *said step of moving the sample to a first location including the step of placing said sample on a first side of a second membrane;*
   *the step of establishing an electrical field between the first location and a third location including the step of establishing an electrical potential between the second side of the second membrane and the second side of the first membrane;*
   *the step of establishing a potential between the first and third locations further including the step of establishing a potential difference between a first buffer solution in intimate contact with the second side of the first membrane and a second buffer solution in intimate contact with the second side of the second membrane, said first and second solutions being insulated from each other;*
   *placing a protective material against the first side of the first membrane, whereby said one molecular species is moved into said protective material and;*
   *continuously passing different portions of said sample through said first location, whereby said one molecular species is continuously moved from a flowing sample.*

5. A method of *separating, concentrating and* removing at least one molecular species from a sample *as a concentrate*, comprising the steps of:

*placing buffer liquid in first and second buffer compartments of an electrode housing wherein the first and second buffer compartments are separated by a separating wall with at least one of the two buffer compartments being open at the top, whereby a sample concentrating cell may be lowered onto the separating wall;*

*lowering the sample concentrating cell onto and mounting it to the separating wall, wherein buffer solution in said first buffer compartment wets a first location of said sample concentrating cell and buffer solution in said second buffer compartment wets a second location of said sample concentrating cell;* moving [the] *said* sample to [a] *said* first location *wherein the sample is spaced from said second location in said sample concentrating cell;* transporting said one molecular species to [a] said second location spaced from the first location on a first side of a membrane having pores sufficiently small to hold said *one* molecular species *through a passageway that communicates between the first and second locations;* said step of transporting said one molecular species including the steps of establishing an electrical field between said first location and a third location spaced a greater distance from said first side of a said membrane than said first location and establishing a path for ion flow between the third location and the second side of said membrane, whereby the one molecular species is moved by electrophoresis from the sample to a position against the first side of the membrane;

removing at least a portion of the [first] *one* molecular species from the first side of the membrane *in concentrated form from said second location as a concentrate;* said step of moving the sample to a first location including the step of placing said sample on a first side of a second membrane; and the step of establishing an electrical field between the first location and a third location including the step of establishing an electrical potential between the second side of the second membrane and the second side of the first-mentioned membrane.

8. A method of *separating, concentrating* and removing at least one molecular species from a sample *as a concentrate*, comprising the steps of:

*placing buffer liquid in first and second buffer compartments of an electrode housing wherein the first and second buffer compartments are separated by a separating wall with at least one of the two buffer compartments being open at the top, whereby a sample concentrating cell may be lowered onto the separating wall;*

*lowering the sample concentrating cell onto and mounting it to the separating wall wherein buffer solution in said first buffer compartment wets a first location of said sample concentrating cell and buffer solution in said second buffer compartment wets a second location of said sample concentrating cell;* moving [the] *said* sample to [a] *said* first location, *wherein the sample is spaced from said second location in said sample concentrating cell;* transporting said one molecular species to [a] *said* second location spaced from the first location on a first side of a membrane having pores sufficiently small to hold said *one* molecular species *through a passageway that communicates between the first and second locations;* said step of transporting said one molecular species including the steps of establishing an electrical field between said first location and a third location spaced a greater distance from said first side of said membrane than said first location and establishing a path for ion flow between the third location and the second side of said membrane, whereby the one molecular species is moved by electrophoresis from the sample to a position against the first side of the membrane;

removing at least a portion of the [first] *one* molecular species from the first side of the membrane *in concentrated form from said second location as a concentrate;* and placing a protective material against the first side of the first-mentioned membrane, whereby said one molecular species is moved into said protective material.

10. A method according to claim 1 in which said one molecular species is drawn from the first side of the membrane after buffer has been withdrawn from said second location, whereby the one molecular species is easily selected for removal.

11. A method according to claim 10 in which the one molecular species is drawn from the first side of the membrane while the first and second membranes are mounted together in a concentrating cell.

12. A method according to claim 1 in which the step of transportating said one molecular species to said second location includes the step of transporting said one molecular species from a first portion of the sample concentrating cell at the first location to a second portion of the sample concentrating cell at the second location that has a lower volume than the first volume.

13. A method in accordance with claim 12 in which the step of transporting said one molecular species includes the step of transporting said one molecular species through a buffer solution in the passageway connecting the first location to the second location.

14. *A method of separating, concentrating and removing at least one molecular species from a sample as a concentrate, comprising the steps of:*

*placing buffer liquid in first and second buffer compartments of an electrode housing wherein the first and second buffer compartments are separated by a separating wall with at least one of the two buffer compartments being open at the top, whereby a sample concentrating cell may be lowered onto the separating wall;*

*lowering the sample concentrating cell onto and mounting it to the separating wall wherein buffer solution in said first buffer compartment wets a first location of said sample concentrating cell and buffer solution in said second buffer compartment wets a second location of said sample concentrating cell;*

*moving said sample to said first location wherein the sample is spaced from said second location in said sample concentrating cell;*

*transporting said one molecular species to said second location spaced from the first location on a first side of a membrane having pores sufficiently small to hold said one molecular species through a passageway that communicates between the first and second locations;*

*said step of transporting said one molecular species including the steps of establishing an electrical field between said first location and a third location spaced a greater distance from said first side of said mem-* brane than said first location and establishing a path for ion flow between the third location and the second side of said membrane, whereby the one molecular species is moved by electrophoresis from the sample to a position against the first side of the membrane;

removing at least a portion of the one molecular species from the first side of the membrane in concentrated form from said second location as a concentrate;

said step of moving the sample to a first location including the step of placing said sample on a first side of a second membrane;

the step of establishing an electrical field between the first location and a third location including the step of establishing an electrical potential between the second side of the second membrane and the second side of the first membrane; and the step of removing the concentrate including the step of lifting the sample concentrating cell from the separating wall and drawing the concentrate from the first side of the membrane.

15. A method according to claim 14 in which the step of mounting a sample concentrate cell includes the step of mounting a sample concentrator cell with the first and second section adapted to be positioned substantially horizontally from each other when it is mounted to the separating wall; wherein the one molecular species may be moved substantially horizontally from the first location to the second location.

16. A method according to claim 1 in which the step of removing at least a portion of the first molecular species from the first side of the membrane includes the steps of:

lifting the concentrating cell up from the separating wall and out of the electrode housing after concentration of the molecular species; and removing the molecular species from the sample concentrating cell after concentration by removing a portion of liquid lying against the first side of the first membrane.

* * * * *